(12) United States Patent
Frost

(10) Patent No.: US 7,977,450 B2
(45) Date of Patent: Jul. 12, 2011

(54) SYNTHESIS OF CAPROLACTAM FROM LYSINE

(75) Inventor: John W. Frost, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 462 days.

(21) Appl. No.: 12/147,256

(22) Filed: Jun. 26, 2008

(65) Prior Publication Data

US 2009/0005532 A1 Jan. 1, 2009

Related U.S. Application Data

(60) Division of application No. 11/635,373, filed on Dec. 7, 2006, now Pat. No. 7,399,855, which is a continuation of application No. PCT/US2005/020326, filed on Jun. 9, 2005.

(60) Provisional application No. 60/578,620, filed on Jun. 10, 2004.

(51) Int. Cl.
C08G 69/16 (2006.01)
C07D 201/08 (2006.01)

(52) U.S. Cl. .................... 528/323; 540/528; 540/533

(58) Field of Classification Search .............. 528/323; 540/528, 533
See application file for complete search history.

(56) References Cited

U.S. PATENT DOCUMENTS

| | | | |
|---|---|---|---|
| 2,142,007 A | 12/1938 | Schlack | |
| 2,241,321 A | 5/1941 | Schlack | |
| 2,979,439 A | 4/1961 | Kinoshita et al. | |
| 3,018,273 A | 1/1962 | Butler et al. | |
| 3,625,923 A | 12/1971 | Roberts | |
| 3,687,810 A | 8/1972 | Kurihara et al. | |
| 3,707,441 A | 12/1972 | Shiio et al. | |
| 3,862,262 A | 1/1975 | Hendrick et al. | |
| 3,871,960 A | 3/1975 | Kubota et al. | |

(Continued)

FOREIGN PATENT DOCUMENTS

DE 748253 6/1938

(Continued)

OTHER PUBLICATIONS

Belyaev, A novel synthetic route to enantiomers of E-hydroxynorleucine and E-chloronorleucine from L- and D,L-lysine, Tetrahedron Lett. 36(3):439-440 (1995).

(Continued)

Primary Examiner — Randy Gulakowski
Assistant Examiner — Rachel Kahn
(74) Attorney, Agent, or Firm — Greenberg Traurig, LLP; Jennifer A. Camacho; Fang Xie

(57) ABSTRACT

In various embodiments, the present invention can involve a method of synthesizing α-amino-ε-caprolactam. The method can comprise heating a salt of L-lysine in a solvent comprising an alcohol. In other embodiments, the present invention can involve methods for synthesizing ε-caprolactam. The methods can comprise heating a salt of L-lysine in a solvent comprising an alcohol and deaminating the reaction product. In various embodiments, the invention can include methods of converting biomass into nylon 6. The methods can comprise heating L-lysine in a solvent comprising an alcohol to produce α-amino-ε-caprolactam, deaminating to produce ε-caprolactam and polymerizing into nylon 6, wherein the L-lysine is derived from the biomass. In other embodiments, the present invention can include methods of making nylon 6. The methods can comprise synthesizing ε-caprolactam and then polymerizing, wherein the ε-caprolactam is derived from L-lysine.

18 Claims, 1 Drawing Sheet

U.S. PATENT DOCUMENTS

| | | |
|---|---|---|
| 3,925,325 A | 12/1975 | Heimsch et al. |
| 3,965,375 A | 6/1976 | Bergman, Jr. et al. |
| 4,022,683 A | 5/1977 | Bludis et al. |
| 4,031,164 A | 6/1977 | Hedrick et al. |
| 4,034,015 A | 7/1977 | Hedrick et al. |
| RE30,371 E | 8/1980 | Hedrick et al. |
| 4,223,112 A | 9/1980 | Hedrick et al. |
| 4,275,157 A | 6/1981 | Tosaka et al. |
| 4,368,115 A | 1/1983 | Chianelli et al. |
| 4,411,997 A | 10/1983 | Shimazaki et al. |
| 4,465,790 A | 8/1984 | Quayle |
| 4,520,021 A | 5/1985 | Harris et al. |
| 4,601,829 A | 7/1986 | Kaneko et al. |
| 4,615,742 A | 10/1986 | Wright |
| 4,617,090 A | 10/1986 | Chum et al. |
| 4,623,623 A | 11/1986 | Nakanishi et al. |
| 4,692,520 A | 9/1987 | Van Geenen et al. |
| 4,706,903 A | 11/1987 | Brink et al. |
| 4,716,142 A | 12/1987 | Laine et al. |
| 4,739,064 A | 4/1988 | Shaw |
| 4,740,487 A | 4/1988 | Matheson et al. |
| 4,752,579 A | 6/1988 | Arena et al. |
| 4,787,939 A | 11/1988 | Barker et al. |
| 4,826,819 A | 5/1989 | Vecchietti et al. |
| 4,861,722 A | 8/1989 | Sano et al. |
| 4,908,312 A | 3/1990 | Ozaki et al. |
| 4,954,441 A | 9/1990 | Katsumata et al. |
| 4,959,452 A | 9/1990 | Meyer et al. |
| 4,963,486 A | 10/1990 | Hang |
| 5,032,664 A | 7/1991 | Frauendorf et al. |
| 5,047,332 A | 9/1991 | Chahal |
| 5,177,009 A | 1/1993 | Kampen |
| 5,221,357 A | 6/1993 | Brink |
| 5,236,831 A | 8/1993 | Katsumata et al. |
| 5,250,423 A | 10/1993 | Murakami et al. |
| 5,252,199 A | 10/1993 | Singhal et al. |
| 5,258,300 A | 11/1993 | Glassman et al. |
| 5,278,121 A | 1/1994 | Singhal et al. |
| 5,409,600 A | 4/1995 | Weissman et al. |
| 5,628,830 A | 5/1997 | Brink |
| 5,639,744 A | 6/1997 | Marchi et al. |
| 5,650,304 A | 7/1997 | Ishii et al. |
| 5,798,237 A | 8/1998 | Picataggio et al. |
| 5,807,870 A | 9/1998 | Anderson et al. |
| 5,840,358 A | 11/1998 | Höfler et al. |
| 5,855,767 A | 1/1999 | Powers et al. |
| 5,868,851 A | 2/1999 | Lightner |
| 6,022,419 A | 2/2000 | Torget et al. |
| 6,096,885 A | 8/2000 | Dezube et al. |
| 6,162,351 A | 12/2000 | Sudhakar et al. |
| 6,228,177 B1 | 5/2001 | Torget |
| 6,267,874 B1 | 7/2001 | Iijima et al. |
| 6,379,934 B1 | 4/2002 | Tilg et al. |
| 6,403,844 B1 | 6/2002 | Zhang et al. |
| 6,504,047 B2 | 1/2003 | Knaup |
| 6,610,530 B2 | 8/2003 | Blank et al. |
| 6,620,292 B2 | 9/2003 | Wingerson |
| 6,670,156 B1 | 12/2003 | Möckel et al. |
| 6,692,578 B2 | 2/2004 | Schmidt et al. |
| 7,112,312 B2 | 9/2006 | Chou |
| 2001/0056184 A1 | 12/2001 | Noda et al. |
| 2006/0258638 A1 | 11/2006 | Olson et al. |

FOREIGN PATENT DOCUMENTS

| | | |
|---|---|---|
| GB | 1067153 | 5/1967 |
| JP | 59-76063 | 4/1984 |
| JP | H03-17062 | 1/1991 |
| JP | 03-176474 | 7/1991 |
| JP | 2003/145933 | 5/2003 |
| JP | 2003-206276 | 7/2003 |
| WO | 2005/123669 | 12/2005 |
| WO | 2007/017610 | 2/2007 |
| WO | 2007/101867 | 9/2007 |
| WO | 2008/103366 | 8/2008 |

OTHER PUBLICATIONS

Blade-Font, Facile synthesis of γ-, δ-, and ε-lactams by cyclodehydration of ω-amino acids on alumina or silical gel, Tetrahedron Lett. 21:2443-2446 (1980).

Doldouras et al., A direct, selective, and general method for reductive deamination of primary amines, J. Am. Chem. Soc. 100:341-342 (1978).

Egorova et al., On the role of β hydrogen atoms in the hydrodenitrogenation of 2-methylpyridine and 2-methylpiperidine, J. Catalysis 206:263-271 (2002).

Eijsbouts et al., Periodic trends in the hydrodenitrogenation activity of carbon-supported transition metal sulfide catalysts, J. Catalysis 109:217-220 (1988).

Goto et al., Synthesis of 2-amino-β-caprolactam by cyclodehydration of lysine in subcritical water, J. Chem. Eng. of Japan 37(2):353-356 (2004).

Guttieri et al., Selective cleavage of carbon-nitrogen bonds with platinum, J. Org. Chem. 49:2875-2880 (1984).

Ho, Hydrodenitrogenation catalysis, Catal. Rev. Sci. Eng. 30(1):117-160 (1988).

Kamm et al., Biorefinery—Systems, Chem. Biochem. Eng. Q. 18(1):1-6 (2004).

Ledoux et al., Hydrodenitrogenation activity and selectivity of well-dispersed transition metal sulfides of the second row on activated carbon, J. Catalysis 115:580-590 (1989).

Metelkina et al., Reaction of metal alkoxides with lysine: substitution of alkoxide ligands vs. lactam formation, Monatshefte für Chemie 134:1065-1069 (2003).

Mochida et al., An overview of hydrodesulfurization and hydrodenitrogenation, Japan Pet. Inst. 47(3):145-163 (2004).

Pellegata et al., An improved sysnthesis of γ-, δ-, and ε-lactams, Synthesis, 614-616 (1978).

Ramamurthy et al., An improved synthesis of carbon-14 labelled carboxylic acids from carbon-14 labelled amino acids, J. Labelled Compd. Rad. 25(8):809-814 (1988).

Rota et al., Role of hydrogenolysis and nucleophilic substitution in hydrodenitrogenation over sulfided NiMo/γ- Al2O3 , J. Catalysis 202:195-199 (2001).

Rota et al., Stereochemistry of hydrodenitrogenation: the mechanism of elimination of the amino group from cyclohexylamines over sulfided Ni-Mo/γ-Al2O3 catalysts, J. Catalysis 200:389-399 (2001).

Thomsen et al., Manufacturing of stabilised brown juice for L-lysine production—from university lab scale over pilot scale to industrial production, Chem. Biochem. Eng. Q. 18(1):37-46 (2004).

Vit et al., Simultaneous hydrodenitrogenation of pyridine and hydrodesulfurization of thiophene over carbon-supported platinum metal sulfides, J. Catalysis 119:1-7 (1989).

Zhang et al., Aqueous-phase hydrogenation of lactic acid to porpylene glycol, Appl. Catal. A-Gen. 219:89-98 (2001).

Zhang et al., Kinetics of aqueous hydrogenation of lactic acid to propylene glycol, Ind. Eng. Chem. Res. 41:691-696 (2002).

Zhao et al., Investigation of the mechanism of the hydrodenitrogenation of n-hexylamines over sulfided NiMo/γ-Al2O3, J. Catalysis 221:441-454 (2004).

Zhao et al., Mechanisms of the hydrodenitrogenation of alkylamines with secondary and tertiary α-carbon atoms on sulfided NiMo/Al2O3, J. Catalysis 222:532-544 (2004).

Zhao, Mechanisms of hydrodenitrogenation of amines over sulfided NiMo, CoMo, and Mo supported on Al2O3, (doctoral dissertation; Swiss Federal Institute of Technology, Zurich), http://e-collection.ethbib.ethz.ch/ecol-pool/diss/fulltext/eth15555.pdf (2004).

Angelucci, Luciano, et al., "Synthesis and amnesia-reversal activity of a series of 7- and 5-membered 3-acylamino lactams," Journal of Medicinal Chemistry, vol. 36, No. 11, pp. 1511-1519, (1993).

Achkar, Jihane, et al., "Biosynthesis of Phloroglucinol," Journal of the American Chemical Society, vol. 127, pp. 5332-5333, (2005).

Anastassiadis, Savas, "L-Lysine Fermentation," Recent Patents on Biotechnology, vol. 1, pp. 11-24, (2007).

Beech J.S., et al., "Neuroprotection in ischemia-reperfusion injury: an antiinflammatory approach using a novel broad-spectrum chemokine inhibitor," Journal Cerebral Blood Flow & Metabolism, vol. 21, pp. 683-689, (2001).

Beech J.S., et al., "The MHP36 Line of Murine Neural Stem Cells Expresses Functional CXCR1 Chemokine Receptors that Initiate Chemotaxis In Vitro," Journal of Neuroimmunology, vol. 184, pp. 198-208, (2007).

Chen, M.S., et al., "The Structure of Catalytically Active Gold on Titania," Science, vol. 306, pp. 252-255, (2004).

Corma, A., et al., "Chemoselective Hydrogenation of Nitro Compounds with Supported Gold Catalysts," Science, vol. 313, pp. 332-334, (2006).

Couty, F., "Asymmetric Syntheses of Pipecolic Acid and Derivatives," Amino Acids, vol. 16, No. 3-4, pp. 297-320, (1999).

Fox, David J., et al., "Design, Synthesis and Preliminary Pharmacological Evaluation of N-Acyl-3-aminoglutarimides as Broad-Spectrum Chemokine Inhibitors in Vitro and Anti-inflammatory Agents in Vivo," Journal of Medicinal Chemistry, vol. 45, pp. 360-370, (2002).

Fox, David J., et al., "Identification of 3-(Acylamino)azepan-2-ones as Stable Broad-Spectrum Chemokine Inhibitors Resistant to Metabolism in Vivo," Journal of Medicinal Chemistry, vol. 48, No. 3, pp. 867-874, (2005).

Frow, E.K., et al., "Tools for Anti-Inflammatory Drug Design: In Vitro Models of Leukocyte Migration," Meddicinal Research Reviews vol. 24, No. 3, pp. 267-298, (2004).

Grainger, D.J., et al., "Broad Spectrum Chemokine Inhibitors Related to NR58-3.14.3," Mini-Reviews in Medicinal Chemistry, vol. 5, pp. 825-832, (2005).

Grainger, D.J., et al., "Blockade of chemokine-induced signaling inhibits CCR5-dependent HIV infection in vitro without blocking gp 120/CCR5 interaction," Retrovirology, vol. 2, p. 1-9, (2005).

Grainger, D.J., et al., "Broad-spectrum chemokine inhibitors (BSCIs) and their anti-inflammatory effect in vivo," Biochemical Pharmacology., vol. 65, pp. 1027-1034, (2003).

Heitman, J., et al., "Targets for Cell Cycle Arrest by the Immunosuppressant Rapamycin in Yeast," Science, vol. 253, pp. 905-909, (1991).

Katho, A. et al., "Determination of Ornithine and Lysine by Visible Spectrophotometry," Analytical Letters, vol. 26, No. 1, pp. 73-86, (1993).

Kisfaludy, Lajos, et al., "One-step synthesis of L-piperidine-2-carboxylic acid," vol. 2, p. 163, (1982).

Lankey, R. L. and Anastas, P. T. (ed.), "Sustainability Through Green Chemistry and Engineering," ACS Symposium Series, 823, American Chemical Society, Washington, D.C., (2002).

Matsuguma et al., "Hydropxylamine-O-Sulfonic Acid," Inorganic Syntheses vol. 5, pp. 122-125, (1957).

Mosedale, D.E., et al., "Circulating levels of MCP-1 and eotaxin are not associated with presence of atherosclerosis or previous myocardial infarction, "Atherosclerosis., vol. 183, pp. 268-274, (2005).

Naidu, B.V., et al., "Broad-Spectrum Chemokine Inhibition Ameliorates Experimental Obliterative Bronchiolitis," The Annals of Thoracic Surgery, vol. 75, No. 4, pp. 1118-1122, (2003).

Ohtani, Bunsho, et al., "Titanium(IV) oxide photocatalyst of ultra-high activity for selective N-cyclization of an amino acid in aqueous suspensions," Chemical Physical Letters, vol. 242, No. 3, pp. 315-319, (1995).

Ohtani, Bunsho, et al., "Photocatalytic Racemization of Amino Acids in Aqueous Polycrystalline Cadmium(II) Sulfide Dispersions," Journal of the Chemical Society, vol. 91, No. 7, XP000497529, pp. 1103-1109, Apr. 7, (1995).

Ohtani, Bunsho, et al., "Photocatalytic One-Step Syntheses of Cyclic Imino Acids by Aqueous Semiconductor Suspensions," Journal of Organic Chemistry, vol. 55, No. 21, XP002500194, pp. 5552-5553, (1990).

Pal, B., et al., "Photocatalytic redox-combined synthesis of L-pipecolinic acid from L-lysine by suspended titania particles: effect of noble metal loading on the selectivity and optical purity of the product," Journal of Catalysis, vol. 217, pp. 152-159, (2003).

Paruszewski, R., et al., "Amino acid derivatives with anticonvulsant activity," Chem. Pharm. Bull., vol. 49, pp. 629-631, (2001).

Reckless, J., et al., "Broad-Spectrum Chemokine Inhibition Reduces Vascular Macrophage Accumulation and Collagenolysis Consistent With Plaque Stabilization in Mice," Journal of Vascular Research, vol. 42, pp. 492-502, (2005).

Reckless, J., et al., "Identification of oligopeptide sequences which inhibit migration inducted by a wide range of chemokines.", Biochemistry Journal., vol. 15, pp. 340 (pt.3), p. 803-811, (1999).

Reckless, J., et al., "The pan-chemokine inhibitor NR58-3.14.3 abolishes TNF-alpha accumulation and leukocyte recruitment inducted by lipopolysaccharide in vivo," Immunology, vol. 103, pp. 244-254, (2001).

Schendel, Frederick J., et al., "Production at 50° C. by Mutants of a Newly Isolated and Characterized Methylotrophic Bacillus sp," Applied and Environmental Microbiology, vol. 56, No. 4, pp. 963-970, (1990).

Schroff, R.W., et al., "The toxicology of chemokine inhibition," Mini-Reviews in Medicinal Chemistry, vol. 5, pp. 849-855, (2005).

Shuker, S.B., et al., "Discovering high-affinity ligands for proteins: SAR by NMR," Science, vol. 274, pp. 1531-1534, (1996).

Skerritt, J.H., et al., "Differential modulation of gamma-aminobutyric acid receptors by caprolactam derivatives with central nervous system depressant or convulsant activity," Brain Research, vol. 331, No. 2, pp. 225-233, (1985).

Takei, Go, et al., "Photocatalytic redox-combined synthesis with Ti02 film modified microchannel," Special Publication—Royal Society of Chemistry, vol. 1, pp. 93-95, (2004).

Wilbert, S.M., et al., "Quantitative analysis of a synthetic peptide, NR58-3.14.3, in serum by LC-MS with inclusion of a diastereomer as internal standard," Analytical Biochemistry, vol. 278, No. 1, pp. 14-21, (2000).

Williams, M.F., "Sulfur and Nitrogen sensitivity of Supported Pt-Hydrogenation Catalysts," Doctoral Dissertation, Technische Universität München, (2005).

International Search Report for International App. No. PCT/US2005/020326 (3 pages).

International Preliminary Report on Patentability for International App. No. PCT/US2005/020326 (5 pages).

Presentation of Information from Japanese application No. 2007-527729.

SYNTHESIS OF CAPROLACTAM FROM LYSINE

CROSS-REFERENCE TO RELATED APPLICATIONS

This application is a divisional of U.S. application Ser. No. 11/635,373, filed on Dec. 7, 2006, now U.S. Pat. No. 7,399,855 which claims priority to International Application No. PCT/US2005/020326, filed on Jun. 9, 2005, which claims the benefit of U.S. Provisional Application No. 60/578,620, filed on Jun. 10, 2004, both of which are incorporated herein by reference.

FIELD OF THE INVENTION

The present invention relates to a method of synthesizing a caprolactam, and more specifically, synthesizing $\epsilon$-caprolactam from L-lysine.

BACKGROUND

About 2.5 billion tons of nylon 6 is produced annually on a worldwide basis. The production of nylon 6 is accomplished by the ring opening polymerization of the monomer $\epsilon$-caprolactam. The starting chemical compound for the production of $\epsilon$-caprolactam is benzene which is converted to either cyclohexane or phenol and either chemical is converted via cyclohexanone to cyclohexanone oxime and then this intermediate is heated in sulfuric acid. This chemical reaction is known as the Beckman rearrangement. The starting chemical benzene is produced via the refinement of petroleum chemicals.

SUMMARY

The inventors herein have succeeded in devising a new approach in the production of $\epsilon$-caprolactam from natural products. The approach is based upon the use of L-lysine in a novel process to produce $\epsilon$-caprolactam which is needed as a precursor to nylon 6.

Thus, in various embodiments, the present invention provides a method of synthesizing $\alpha$-amino-$\epsilon$-caprolactam, comprising heating a salt of L-lysine in a solvent comprising an alcohol. In various embodiments, the methods comprise heating a salt of L-lysine in a solvent comprising an alcohol, and deaminating the reaction product. In various embodiments, the invention includes methods of converting biomass into nylon 6. Such methods comprise heating L-lysine in a solvent comprising an alcohol to produce $\alpha$-amino-$\epsilon$-caprolactam, deaminating to produce $\epsilon$-caprolactam and polymerizing into nylon 6, wherein the L-lysine is derived from the biomass.

BRIEF DESCRIPTION OF THE DRAWINGS

The present invention will become more fully understood from the detailed description and the accompanying drawings, wherein.

Figure 1:
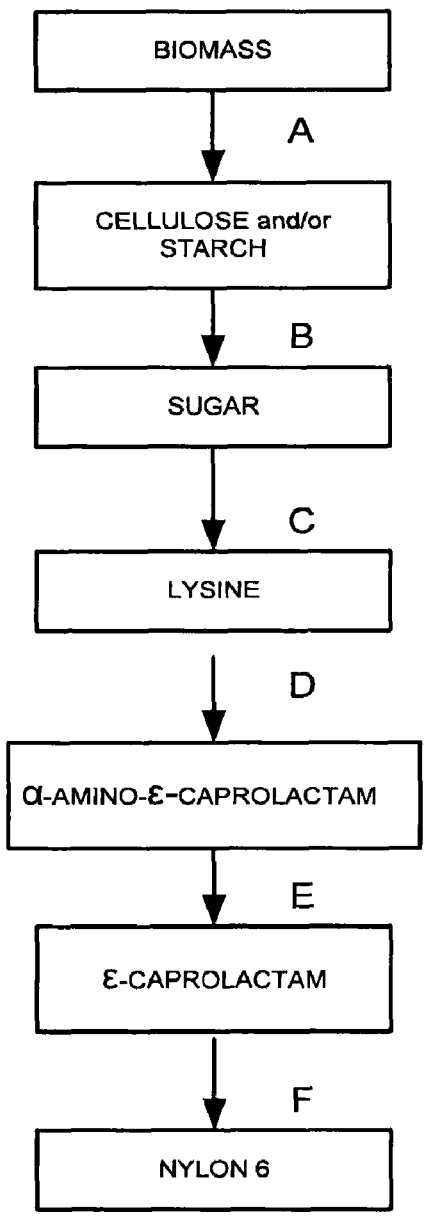
FIG. 1 is a block diagram of a process of converting biomass into nylon 6.

It should be noted that these figures are intended to exemplify the general characteristics of the invention for the purpose of the description of such embodiments herein. These figures may not precisely reflect the characteristics of any given embodiment and is not necessarily intended to define or limit specific embodiments within the scope of this invention.

DETAILED DESCRIPTION

The following definitions and non-limiting guidelines must be considered in reviewing the description of this invention set forth herein. The headings (such as "Introduction" and "Summary,") and sub-headings (such as "Amplification") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

Caprolactam is primarily used in the manufacture of synthetic fibers, especially nylon 6 that is also used in bristle brushes, textile stiffeners, film coatings, synthetic leather, plastics, plasticizers, vehicles, cross linking for polyurethanes, and in the synthesis of lysine. The starting point for the production of $\epsilon$-caprolactam is benzene which is refined from the non-renewable source of petroleum. In addition to its limitations due to its source of non-renewable petroleum, exposure to benzene, which has been linked to acute myeloid leukemia and non-Hodgkin's lymphoma, is a continuing problem for the chemical industry. The most effective way of dealing with benzene's human health risk is to eliminate its use. Such a far reaching solution requires the elaboration of fundamentally new synthesis for chemicals derived from benzene. A sugar such as a non-toxic glucose may be a new starting point for many of these syntheses. In order to use glucose as a replacement for benzene as a starting point for many of these syntheses, a bio-refinery is needed. A biorefinery is a facility that integrates biomass conversion processes and equipment to produce fuels, power and chemicals from biomass. The bio-refinery concept is analogous to a petroleum refinery which produces multiple fuels and products from petroleum. By producing multiple products, a bio-refinery can take advantage of the differences in biomass components and intermediates and maximize the value derived from the biomass feed stock with minimal waste and emissions. The conversion of biomass into a sugar such as glucose is well known in the art (see Advancing Sustainability Through Green Chemistry and Engineering, ACS Symposium Series, 823, edited by Lanky, R. L. and Anastas, P. T., American Chemical Society, Washington, D.C., 2002; Biomass for Energy, Industry and Environment, 6th European Community Conference, edited by Grassi, G., Collina, A. and Zibetta, H., Elsevier Science Publishing Co., Inc., New York, 1998; Biobased Industrial Products: Research and Commercialization Priorities, edited by Dale, B. E., Natural Research Council, Washington, D.C., 1999; Emerging Technologies for Materials and Chemicals from Biomass, ASC Symposium 467, edited by Narayan, R., Rowell, R., Schultz, T., American Chemical Society, Washington, D.C., 1991).

In the early 1960's, Japanese biotechnology firms discovered a bacterial fermentation technique which started with a sugar and produced lysine. L-lysine is produced and available from many industrial sources including such companies as Aginomoto, Kyowa Hakko, Sewon, Arthur Daniels Midland, Cheil Jedang, BASF, and Cargill.

The cyclization of L-lysine to form a seven member ring of α-amino-ε-caprolactam has been attempted before and reports have shown low yields. Such attempts have included reactions in near super critical water (see Japanese Patent No. 2003206276 to Goto et al. issued Jul. 22, 2003) or reactions using an excess of $Al_2O_3$ in toluene (see Blade-Font, A., Tetrahedron Lett., 1980, 21, 2443-2446. Pellegata, R., Pinza, M.: Pifferi G., Synthesis 1978, 614-616).

In one aspect, the invention provides an efficient route for the cyclization for a cyclic amidation reaction to form lactams having ring sizes from 5 to 8 ring members. Following cyclic amidation, other reactive groups on the cyclic ring may be removed if desired. In one aspect, the invention provides efficient cyclic amidation carried out in an alcohol solvents having from 2 to 6 carbons. Amino functional carboxylic acid useful in the invention improves those that can cyclize to form a stable lactam, preferably one having from 5 to 8 ring members. The amino functional carboxylic acids can contain other functional groups as long as those functional groups do not interfere with the amidation reaction mediated by the 2 to 6 carbon alcohol solvent.

According to the present invention, a new process for the cyclization of L-lysine to α-amino-ε-caprolactam is described herein. In addition, in accordance with the present invention, a process for the deamination of α-amino-ε-caprolactam to ε-caprolactam is described herein. Commercially available sources of L-lysine such as, but not limited to, L-lysine dihydrochloride, L-lysine hydrochloride, L-lysine phosphate, L-lysine diphosphate, L-lysine acetate, and L-lysine may be used and any needed steps so that the L-lysine is in the proper state for the following reactions will be known by one skilled in the art. In addition, commercially available sources of lysine maybe used but a step to separate the L-lysine from the D-lysine may be added such as, for an example, a chiral separation step and such separation and purification techniques will be known by one skilled in the art. In various embodiments, a cyclization reaction was initiated after neutralization of lysine hydrochloride with sodium hydroxide (NaOH). In this embodiment, the resulting NaCl is precipitated out of the solution and is removed by filtration after the cyclization reaction is completed. In various embodiments, water that is generated during the cyclization reaction may be removed using a Dean-Stark trap. Other methods known within the art may be used to remove the water such as evaporation, crystallization, distillation or any other appropriate method known by one skilled in the art. In various embodiments of the invention, water is removed as an azeotrope. In various embodiments of the invention, the neutralized L-lysine is heated in an alcohol. In various other embodiments of the invention, the neutralized L-lysine is heated in the presence of an alcohol and a catalyst. In some embodiments of the invention, the alcohol has about 2 to about 6 carbons.

Non-limiting examples of alcohols include 1-propanol, 2-propanol, 1-butanol, 2-butanol, isobutanol, 1,2-propanediol, 1,3-propanediol, 1,2-butanediol, 1,4-butanediol, all isomers of 5 carbon monols, diols and triols including without limitation 1-pentanol, 1,2-pentanediol, 1,5-pentanediol, and all isomers of 6 carbon monodiols, diols and triols including without limitation, 1-hexanol, 1,2-hexanediol, 1,6-hexanediol. Other non-limiting examples of 2 to 6 carbon alcohols include glycerol, trimethylolpropane, pentaerythritol and the like. In various embodiments, the alcohols have a single hydroxyl group. In other embodiments, the alcohols have 2 hydroxyl groups. In some embodiments, the alcohols have 3 hydroxyl groups. Non-limiting examples of glycols include propylene glycol, butylene glycol, neopentyl glycol and the like.

In some embodiments of the invention, the catalyst is aluminum oxide ($Al_2O_3$). In various embodiments of the invention, the heating of the neutralized L-lysine in the alcohol is accomplished by reflux. In various embodiments of the invention, the heating of the alcohol and the neutralized lysine in the presence of a catalyst is accomplished by reflux. In various embodiments, the heating is at a high enough temperature to allow azeotropic removal of water with the alcohol. In various embodiments, the heating is below a temperature that polymerizes the caprolactam. In some embodiments, the heating is at temperatures from about 99° C. to about 201° C. In a preferred embodiment of the invention, the alcohol is 1,2-propanediol. In addition to the higher yields by the use of the 1,2-propanediol, this organic alcohol may be readily available at a bio-refinery since it may be obtained by the hydrogenation of lactic acid which may be readily available as a co-product produced from the biomass. The following are some non-limiting examples based on reaction (1).

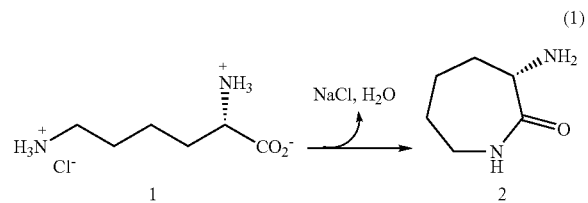

(1)

Example 1

A stirred mixture of L-lysine hydrochloride 1 (55 g, 300 mmol) and NaOH (12 g, 300 mmol) in hexanol (1.2 L) is heated to reflux with a Dean-Stark trap used to remove $H_2O$. The suspension is refluxed for 8 hours until all starting material is consumed (which maybe determined by 1H NMR). The suspension is then cooled and filtered to remove byproduct NaCl. The filtrate is concentrated and the resulting crude α-amino-ε-caprolactam 2 is dissolved in water. After acidification to pH 6 with addition of concentrated HCl and partial concentration, crystals maybe formed at room temperature to afford α-amino-ε-caprolactam hydrochloride (37 g) in 75% yield.

Example 2

A stirred mixture of L-lysine hydrochloride 1 (55 g, 300 mmol) and NaOH (12 g, 300 mmol) in 1,2-propanediol (1.2 L) is heated to reflux. A Dean-Stark trap is used to withdraw the first 120 mL of condensed solvent. The reaction solution is refluxed for an additional 2 hours until all starting material is consumed (which maybe determined by 1H NMR). The solution is cooled and is concentrated under vacuum. Ethanol is used to completely dissolve the α-amino-ε-caprolactam 2. Byproduct NaCl is removed by filtration. The filtrate is concentrated and the resulting crude α-amino-ε-caprolactam 2 is dissolved in water. After acidification to pH 6 with addition of concentrated HCl and subsequent partial concentration, crystals maybe formed at room temperature to afford α-amino-ε-caprolactam hydrochloride (36.5 g) in 74% yield.

Example 3

50 mmols of L-lysine hydrochloride 1 is neutralized with 50 mmols of NaOH and then 200 ml of ethanol is added. This mixture is heated to 200° C. for eight hours. The yield of α-amino-ε-caprolactam 2 produced by this reaction is about 47%.

Example 4

30 mmols of L-lysine hydrochloride 1 is neutralized with 30 mmols of NaOH and then 120 ml of 1-pentanol is added. This mixture is heated to 137° C. and is refluxed for 60 hours. The yield of α-amino-ε-caprolactam 2 produced by this reaction is about 93%.

Example 5

30 mmols of L-lysine hydrochloride 1 is neutralized with 30 mmols of NaOH and then 120 ml of 1-hexanol is added. This mixture is heated to 157° C. and is refluxed for 8 hours. The yield of α-amino-ε-caprolactam 2 produced by this reaction is about 89%.

Example 6

300 mmols of L-lysine hydrochloride 1 is neutralized with 300 mmols of NaOH and then 1.2 L of 1-hexanol is added. This mixture is heated to 150° C. and is refluxed for 8 hours. The yield of α-amino-ε-caprolactam 2 produced by this reaction is about 91%.

Example 7

300 mmols of L-lysine hydrochloride 1 is neutralized with 300 mmols of NaOH and then 1.2 L of 1,2-propanediol is added. This mixture is heated to 187° C. and is refluxed for 2 hours after removing about the 10% of the solvent when the reaction is first brought to reflux. The yield of α-amino-ε-caprolactam 2 produced by this reaction is about 96%.

Example 8

30 mmols of L-lysine hydrochloride 1 is neutralized with 30 mmols of NaOH and then 270 mmols of $Al_2O_3$ is added, followed by the addition of 120 ml of 1-butanol. This mixture is heated to 117° C. and is refluxed for six hours. The yield of α-amino-ε-caprolactam 2 produced by this reaction is about 92%.

Example 9

30 mmols of L-lysine hydrochloride 1 is neutralized with 30 mmols of NaOH and then 270 mmols of $Al_2O_3$ is added, followed by 120 ml of 1-pentanol. This mixture is heated to 137° C. and is refluxed for four hours. The yield of α-amino-ε-caprolactam 2 produced by this reaction is about 96%.

Methods for deaminating organic compounds are well known in the art. Deamination processes are chosen depending on the reaction conditions and yield. In various embodiments, deamination may be accomplished by reacting the amino functional intermediate with hydroxylamine-O-sulphonic acid and KOH catalyst. The hydroxylamine-O-sulphonic acid ($NH_2OSO_3H$) may be prepared by the reaction of bis(hydroxylammonium sulfate ($(NH_2OH)_2H_2SO_4$) with fuming sulphuric acid ($H_2SO_4$—$SO_3$) (see Matsuguma et al., Inorg. Syn. 1957, 5, 122-125). In certain embodiments of the invention, the deamination reaction is run after the removal of NaCl after the completion of the cyclization reaction as described above. Deamination reactions using hydroxylamine-O-sulphonic acid have been described before but have produced low yields of ε-caprolactam (see Doldouras, G. A., Kollonitsch, J., J. Am. Chem. Soc. 1978, 100, 341-342; Ramamurthy, T. V., Ravi, S., Viswanathan, K. V. J. Labelled Compd. Rad., 1987, 25, 809-815). In accordance with the present invention, the reaction temperature is lowered to below the freezing point of water during the addition of the hydroxylamine-O-sulphonic acid. In various embodiments of the invention, the temperature is lowered to about −5° C. and in other embodiments, the temperature is lowered to about −20° C. In various embodiments, the amine is washed away with a solvent. The solvent may be water or a mixture of water and a small organic alcohol. In various embodiments of the invention, the solvent is water. The following are non-limiting examples based on reaction 2 using a product created from Example 7 and producing similar yields.

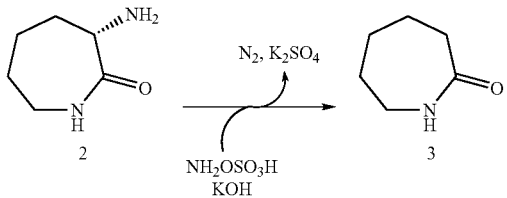

(2)

Example 10

α-Amino-ε-caprolactam 2 (2.56 g, 20 mmol) is dissolved in 100 mL water and the solution cooled to −5° C. After addition of KOH (4.48 g, 80 mmol) followed by NH2OSO3H (4.52 g, 40 mmol), the reaction solution is stirred at −5° C. for 1 h. The reaction solution is then heated to 70-75° C. and is stirred at this temperature for 1 h. The solution is again cooled to −5° C. followed by addition of more KOH (4.48 g, 80 mmol) followed by NH2OSO3H (4.52 g, 40 mmol). After stirring at −5° C. for 1 h, the reaction solution is heated to 70-75° C. and is stirred for another 1 h. After concentration, the crude product is purified by sublimation to give 1.70 g (75%) of colorless, crystalline ε-caprolactam 3.

Example 11

After completion of the cyclization reaction (1) as described above, the NaCl is removed. 20 mmols of α-amino-ε-caprolactam 2 is placed in a reaction chamber and the temperature of the chamber is lowered below the freezing point of water to about −20° C. 800 mmols of KOH is added and then 400 mmols of hydroxylamine-O-sulphonic acid is added. The amine is washed away using a solvent that is 240 ml of water and 160 ml of methanol. The product, ε-caprolactam 3, is then purified by sublimation and the yield is about 61% based on L-lysine starting material.

Example 12

After completion of the cyclization reaction (1) as described above, the NaCl is removed. 20 mmols of α-amino-ε-caprolactam 2 is placed in a reaction chamber and the temperature of the chamber is lowered below the freezing point of water to about −20° C. 800 mmols of KOH is added and then 400 mmols of hydroxylamine-O-sulphonic acid is added. The amine is washed away using a solvent that is 20 ml of water and 80 ml of methanol. The product, ε-caprolactam 3, is then purified by sublimation and the yield is about 62% based on L-lysine starting material.

Example 13

After completion of the cyclization reaction (1) as described above, the NaCl is removed. 20 mmols of α-amino-ε-caprolactam is placed in a reaction chamber and the temperature of the chamber is lowered below the freezing point of water to about −20° C. 800 mmols of KOH is added and then 400 mmols of hydroxylamine-O-sulphonic acid is added. The amine is washed away using a solvent that is 60 ml of water and 40 ml of methanol. The product, ε-caprolactam 3, is then purified by sublimation and the yield is about 64% based on L-lysine starting material.

Example 14

After completion of the cyclization reaction (1) as described above, the NaCl is removed. 20 mmols of α-amino-ε-caprolactam 2 is placed in a reaction chamber and the temperature of the chamber is lowered below the freezing point of water to about −20° C. 160 mmols of KOH is added and then 80 mmols of hydroxylamine-O-sulphonic acid is added. The amine is washed away using a solvent that is 60 ml of water and 40 ml of methanol. The product, ε-caprolactam 3, is then purified by sublimation and the yield is about 65% based on L-lysine starting material.

Example 15

After completion of the cyclization reaction (1) as described above, the NaCl is removed. 20 mmols of α-amino-ε-caprolactam 2 is placed in a reaction chamber and the temperature of the chamber is lowered below the freezing point of water to about −20° C. 160 mmols of KOH is added and then 80 mmols of hydroxylamine-O-sulphonic acid is added. The amine is washed away using a solvent that is 60 ml of water and 40 ml of ethanol. The product, ε-caprolactam 3, is then purified by sublimation and the yield is about 70% based on L-lysine starting material.

Example 16

After completion of the cyclization reaction (1) as described above, the NaCl is removed. 20 mmols of α-amino-ε-caprolactam 2 is placed in a reaction chamber and the temperature of the chamber is lowered below the freezing point of water to about −5° C. 160 mmols of KOH is added and then 80 mmols of hydroxylamine-O-sulphonic acid is added. The amine is washed away using a solvent that is 100 ml of water. The product, ε-caprolactam 3, is then purified by sublimation and the yield is about 75% based on L-lysine starting material.

Referring to FIG. 1, a process of the present invention is illustrated by a block diagram showing biomass being converted into nylon 6. Biomass, as described earlier, which is a material produced by the growth of microorganisms, plants or animals, is supplied to the system. Examples of a biomass include agricultural products and by-products such as corn, husks, stalks, cereal crops, alfalfa, clover, grass clippings, vegetable residues, straw, maize, grain, grape, hemp, sugar cane, flax, and potatoes; forestry and paper products and by-products such as sawdust paper, cellulose, wood pulp, wood chips, pulp sludge and leaves, and other appropriate materials that are known in the art. In various embodiments of the invention, the biomass is high cellulose-containing materials. In other embodiments of the invention, the biomass is high starch-containing materials. In alternative embodiments, the biomass goes through fractionization which yields such components as cellulose, hemicellulose, lignocellulose, plant oil, and/or starch as represented by step A. In various embodiments, the box labeled "Cellulose and/or Starch" may comprise but is not limited to starch, cellulose, hemicellulose, lignocellulose, or combinations thereof and the like. Such separation or fractionization of biomass into cellulose components and/or starch is well known in the art (see U.S. Pat. No. 6,022,419 to Torget et al. issued Feb. 8, 2000; U.S. Pat. No. 5,047,332 to Chahal issued Sep. 10, 1991 and U.S. Pat. No. 6,228,177 to Torget issued May 8, 2001, U.S. Pat. No. 6,620,292 to Wingerson issued Sep. 16, 2003, and B. Kamm and M. Kamm, Biorefinery-Systems, Chem. Biochem. Eng. Q. 18 (1) 1-6 2004). In various embodiments of the invention, the biomass goes through step A can result in a combination of both cellulose components and starch. In various embodiments of the invention, the biomass is not separated but, rather, the biomass moves directly to step B. In step B of FIG. 1, cellulose components, starch, or combinations thereof are converted to a sugar such as glucose by hydrolyzsis. In various embodiments, the box labeled "Sugar" may comprise but is not limited to glucose, dextrose, xylose, sucrose, fructose, arabinose, glycerorol, other sugars or polyols known to one skilled in the art or combinations thereof and the like. In various embodiments of the invention, the raw biomass is converted to a sugar by hydrolization. In various embodiments of the invention, the hydrolyzation is an acid hydrolyzation. In other embodiments of the invention, the hydrolyzation is enzymatic hydrolization. Hydrolyzation methods that could produce a sugar such as glucose are well known in the art (see U.S. Pat. No. 6,692,578 to Schmidt et al. issued Feb. 17, 2004, U.S. Pat. No. 5,868,851 to Lightner issued Feb. 9, 1999, U.S. Pat. No. 5,628,830 to Brink issued May 13, 1997, U.S. Pat. No. 4,752,579 to Arena et al. issued Jun. 21, 1988, U.S. Pat. No. 4,787,939 to Barker et al. issued Nov. 29, 1988, U.S. Pat. No. 5,221,357 to Brink issued Jun. 22, 1993 and U.S. Pat. No. 4,615,742 to Wright issued Oct. 7, 1986).

Depolymerization of hemicellulose produces D-xylose and L-arabinose, which can serve as alternative starting materials for microbial synthesis of chemicals. Plant oils are another component of biomass. Transesterification of plant oils leads to esterified fatty acids which maybe used as biodiesel and glycerol, which is another polyol suitable for use as a starting material in microbial synthesis. In various embodiments of the invention, step B may produce other sugars that may or may not include glucose.

Since the early 1960's, Japanese companies have been perfecting fermentation of L-lysine produced from sugars such as glucose. Unlike human beings and animals, the *Corynebacterium glutamicum* bacterium is able to synthesize lysine. Through classical strain optimization, the bacteria have become able to synthesize large quantities of lysine. Production takes place in fermenters in which the *Corynebacterium glutamicum* bacterium converts raw sugars such as glucose, sugar cane, and/or molasses into lysine. Such processes are well known in the art (see U.S. Pat. No. 2,979,439 to Kinoshita et al. issued Apr. 11, 1961, U.S. Pat. No. 3,687,810 to Kurihara et al. issued Aug. 29, 1972, U.S. Pat. No. 3,707,441 to Shiio et al. issued Dec. 26, 1972, U.S. Pat. No. 3,871,960 to Kubota et al. issued Mar. 18, 1975, U.S. Pat. No. 4,275,157 issued to Tosaka et al. issued Jun. 23, 1981, U.S. Pat. No. 4,601,829 issued to Kaneko issued Jul. 22, 1986, U.S. Pat. No. 4,623,623 issued to Nakanishi et al. issued Nov. 18, 1986, U.S. Pat. No. 4,411,997 issued to Shimazaki et al. issued Oct. 25, 1983, U.S. Pat. No. 4,954,441 issued to Katsumata et al. issued Sep. 4, 1990, U.S. Pat. No. 5,650,304 issued to Ishii et al. issued Jul. 22, 1997, U.S. Pat. No. 5,250,423 issued to Murakami et al. issued Oct. 5, 1993, U.S. Pat. No. 4,861,722 issued to Sano et al. issued Aug. 29, 1989, and Manufacturing of Stabilised Brown Juice for L-lysine Production—from University Lab Scale over Pilot Scale to Industrial Production, M. H. Thomsen et al., Chem. Biochem. Eng. Q. 18 (1) 37-46 (2004).

L-lysine hydrochloride is produced by the treatment of L-lysine solutions with 10% hydrochloric acid to adjust the pH to about 4.5 to about 4.7. It is then heated with activated charcoal at about 80° C. for about 40 minutes to eliminate the color then filtered. The clear filtrate is evaporated under vacuum at about 40° C., cooled and allowed to stand at about 4° C. for about 24 to about 36 hours. The precipitated crystalline L-lysine monochloric acid is separated by filtration and purified by repeated crystallization from ethanol.

Step D is the cyclization of the L-lysine hydrochloric acid to α-amino-ε-caprolactam as described in the present invention from above. Such examples as 1-9 herein and any modifications that would be apparent to one skilled in the art are conditions and reactions for step D. In various embodiments, L-lysine is not converted to L-lysine hydrochloride. In such embodiments, the neutralization step may be omitted from step D. Step E is the deaminization of α-amino-ε-caprolactam to ε-caprolactam as described herein. Examples 10-16 and any modifications that would be apparent to one skilled in the art are reactions that may be used in step E.

The polymerization of ε-caprolactam to nylon 6 is step F and this reaction was invented by Paul Schlack of IG Farben in Germany on about Jan. 28, 1938. The reaction is a ring opening polymerization from the monomer ε-caprolactam which is accomplished by heating the ε-caprolactam to about 250° C. with about 0.3% to about 10% water present. See U.S. Pat. No. 2,142,007 to Schlack issued Dec. 27, 1938 and U.S. Pat. No. 2,241,321 to Schlack issued May 6, 1941. The polymerization of ε-caprolactam to nylon 6 is well known in the art. A non-limiting example of such polymerization is as follows: nylon 6 may be produced by hydrolytic polymerization of caprolactam, with predominant use of the VK tube (abbreviation for the German expression "vereinfacht Kontinuierlich" which means simplified continuous) a heated vertical flow pipe. The molten caprolactam, with 0.3-5% of water, chain length regulators, and, if necessary, a dulling agent, is fed from above, and the polymer melt is discharged at the reactor bottom. Typically the VK tube is equipped with 3 heat exchangers establishing the temperature profile along the reactor. The VK-tube consists of a plug flow zone in the lower part and a mixing/evaporating zone in the top. The function of the top part is to heat up the reaction mass and to evaporate excess water thus setting the total water content in the polymer melt. The endothermic caprolactam ring opening reaction is started, followed by exothermal polyaddition and polycondensation. With the central heat exchanger, the temperature is corrected and equalized over the tube cross section. After passing the central heat exchanger, the temperature rises to about 270-280° C. due to the heat of reaction. The bottom heat exchanger drops the temperature to 240-250° C., thus reaching a higher degree of polymerization in the equilibrium. Simultaneously a higher degree of caprolactam conversion to nylon 6 is achieved. Specifically designed inserts are applied evening out the dwell time over the tube cross section. Sixteen to twenty hours may be the mean dwell time in the tube. Relative solution viscosities from 2.4 to 2.8 are achieved with a single stage process (solvent: 96% sulphuric acid, concentration: 1 g/100 ml, temperature: 25° C.). The maximum capacity may be 130 tonnes/day. In the 2-stage technology, a prepolymerizer, operated under pressure and with high water content, is followed by a final VK polymerizer operated at atmospheric pressure or vacuum. The high reaction rate of the caprolactam ring opening under the conditions in the prepolymerizer yields a low total residence time making the process suitable for very high throughput rates up to 300 tonnes/day.

In various embodiments of the process as described in FIG. 1, additions may be made such that the amine that is a by-product from step E may be recycled so that the nitrogen may be added in step C as a nutrient for fermentation. In other embodiments, the amine that is a by-product in step E may be recycled so that the nitrogen may be added in step B as a nutrient for fermentation. In an alternative embodiment, one skilled in the art may precipitate the monophosphate or diphosphate salt of lysine. The sodium phosphate salt (monobasic or dibasic) generated during cyclization of lysine phosphate maybe (like ammonia above) from step E may be recycled so that the phosphorus may be added in step C as a nutrient for fermentation.

In various embodiments of the invention, a portion of the biomass may be converted into lactic acid and then hydrogenated into 1,2-propanediol which maybe used in Step D. The process of taking biomass and converting it into lactic acid is well known in the art. (See U.S. Pat. No. 6,403,844 to Zhang et al. issued Jun. 11, 2002, U.S. Pat. No. 4,963,486 to Hang issued Oct. 16, 1990, U.S. Pat. No. 5,177,009 issued Kampen issued Jan. 5, 1993, U.S. Pat. No. 6,610,530 issued to Blank et al. issued Aug. 26, 2003, U.S. Pat. No. 5,798,237 issued to Picataggio et al. issued Aug. 25, 1998, and U.S. Pat. No. 4,617,090 to Chum et al. issued Oct. 14, 1986, Zhang, Z; Jackson, J. E.; Miller, D. J. Appl. Catal. A-Gen. 2001, 219, 89-98, Zhang, Z; Jackson, J. E.; Miller, Ind. Eng. Chem. Res. 2002, 41, 691-696).

The examples and other embodiments described herein are exemplary and are not intended to be limiting in describing the full scope of apparatus, systems, compositions, materials, and methods of this invention. Equivalent changes, modifications, variations in specific embodiments, apparatus, systems, compositions, materials and methods may be made within the scope of the present invention with substantially similar results. Such changes, modifications or variations are not to be regarded as a departure from the spirit and scope of the invention. All patents cited herein, as well as, all publications, articles, brochures and product information discussed herein, are incorporated in their entirety herein by reference.

What is claimed is:

1. A method for producing nylon 6, the method comprising:
   (A) heating lysine in a solvent comprising an alcohol, at a temperature of about 99° C. to about 201° C., to produce α-amino-ε-caprolactam;
   (B) deaminating α-amino-ε-caprolactam produced in (A) by a method comprising contacting it at least once with a deamination reagent or catalyst at a temperature below the freezing point of water, to produce ε-caprolactam; and
   (C) polymerizing ε-caprolactam produced in (B) into nylon 6.

2. A method according to claim 1, wherein the lysine comprises L-lysine derived from biomass.

3. A method according to claim 2, wherein the L-lysine is derived by obtaining a sugar from the biomass and converting the sugar into L-lysine.

4. A method according to claim 3, wherein the converting comprises using a fermentation reaction to convert the sugar into L-lysine.

5. A method according to claim 4 further comprising recycling an amine, produced by deamination of α-amino-ε-caprolactam, into the fermentation reaction.

6. A method according to claim 2 further comprising creating lactic acid from the biomass.

7. A method according to claim 6 further comprising hydrogenating the lactic acid to produce 1,2-propanediol.

8. A method according to claim 7 further comprising using the 1,2-propanediol as the alcohol in the heating step (A).

9. A method according to claim 1, wherein the heating (A) comprises heating in the presence of a catalyst.

10. A method according to claim 1, wherein the alcohol used in the heating step (A) has from 2 to 6 carbons.

11. A method according to claim 10, wherein the alcohol comprises a diol.

12. A method according to claim 10, wherein the alcohol comprises a triol.

13. A method according to claim 10, wherein the alcohol comprises a glycol.

14. A method according to claim 10, wherein the alcohol is from the group consisting of ethanol, 1-propanol, 1-butanol, 1-pentanol, 1-hexanol, 1,2-propanediol, and mixtures thereof.

15. A method according to claim 14, wherein the alcohol is 1,2-propanediol.

16. A method according to claim 1, wherein the heating is below the temperature of polymerization of caprolactam.

17. A method according to claim 1, wherein the heating allows the azeotropic removal of water.

18. A method according to claim 1, wherein the heating is accomplished by reflux.

* * * * *

UNITED STATES PATENT AND TRADEMARK OFFICE
CERTIFICATE OF CORRECTION

PATENT NO. : 7,977,450 B2  
APPLICATION NO. : 12/147256  
DATED : July 12, 2011  
INVENTOR(S) : John W. Frost Page 1 of 1

It is certified that error appears in the above-identified patent and that said Letters Patent is hereby corrected as shown below:

In the Specification:  
Column 1, Line 14, before "Field of Invention" insert

--GOVERNMENT LICENSE RIGHTS

This invention was made with government support under CHE0211375 awarded by the National Science Foundation. The government has certain rights in the invention.--

Signed and Sealed this  
Twenty-ninth Day of April, 2014

Michelle K. Lee  
*Deputy Director of the United States Patent and Trademark Office*